United States Patent [19]

Miki et al.

[11] 4,219,507
[45] Aug. 26, 1980

[54] PROCESS FOR PURIFYING ALDEHYDE-CONTAINING KETONES

[75] Inventors: Hisaya Miki; Mitsuki Yasuhara, both of Ichihara, Japan

[73] Assignee: Mitsui Petrochemical Industries Ltd., Tokyo, Japan

[21] Appl. No.: 931,896

[22] Filed: Aug. 8, 1978

[30] Foreign Application Priority Data

Aug. 16, 1977 [JP] Japan .................................. 52-97465

[51] Int. Cl.$^2$ ............................................. C07C 45/24
[52] U.S. Cl. .................................................. 568/411
[58] Field of Search ...................... 260/593 P; 568/881

[56] References Cited

U.S. PATENT DOCUMENTS

| | | | |
|---|---|---|---|
| 2,205,184 | 6/1940 | Woodhouse | 260/593 P |
| 2,543,038 | 2/1951 | McGrath | 260/593 P |
| 3,137,732 | 6/1964 | Kuper | 260/593 P |
| 3,309,407 | 3/1967 | Carpenter et al. | 260/593 P |
| 3,980,718 | 9/1976 | Shabtai et al. | 568/881 |

FOREIGN PATENT DOCUMENTS

| | | | |
|---|---|---|---|
| 2460887 | 7/1975 | Fed. Rep. of Germany | 260/593 |
| 7116417 | 6/1973 | Netherlands | 260/593 |

*Primary Examiner*—N. Morgenstern
*Assistant Examiner*—James H. Reamer
*Attorney, Agent, or Firm*—Sherman & Shalloway

[57] ABSTRACT

A process for purifying an aldehyde-containing ketone, which comprises catalytically hydrogenating a crude ketone containing minor amounts of aliphatic aldehydes at a temperature of from room temperature to about 100° C. and a pressure of from atmospheric pressure to 10 kg/cm$^2$·G, in the presence of hydrogen, a palladium-containing catalyst, and about 0.4 to about 15% by weight, based on the weight of the crude ketone, of an active hydrogen-containing compound having a higher boiling point than the ketone which is selected from the group consisting of water, aliphatic alcohols containing 3 to 7 carbon atoms, aliphatic carboxylic acids containing 1 to 6 carbon atoms, alicyclic alcohols containing 5 to 8 carbon atoms and alkylamines having an alkyl or cycloalkyl group containing 5 to 9 carbon atoms; distilling the hydrogenated product; and recovering a fraction containing the ketone.

11 Claims, No Drawings

PROCESS FOR PURIFYING ALDEHYDE-CONTAINING KETONES

This invention relates to an improved process for purifying a crude ketone containing minor amounts, especially about 50 to about 1000 ppm, of aliphatic aldehydes to form a purified ketone, which comprises pre-treating the crude ketone, then distilling it, and recovering a fraction containing the purified ketone.

More specifically, the invention relates to a process for purifying an aldehyde-containing ketone, which comprises catalytically hydrogenating a crude ketone containing minor amounts of aliphatic aldehydes at a temperature of from room temperature to about 100° C. and a pressure of from atmospheric pressure to 10 kg/cm$^2$·G in the presence of hydrogen, a palladium-containing catalyst, and about 0.4 to about 15% by weight, based on the weight of the crude ketone, of an active hydrogen-containing compound having a higher boiling point than the ketone which is selected from the group consisting of water, aliphatic alcohols containing 3 to 7 carbon atoms, alicyclic alcohols containing 5 to 8 carbon atoms, aliphatic carboxylic acids containing 1 to 6 carbon atoms and alkylamines having an alkyl or cycloalkyl group containing 5 to 9 carbon atoms; distilling the hydrogenated product; and recovering a fraction containing the ketone.

It is well known that a crude ketone obtained by acid-cleaving an alkyl hydroperoxide of the formula

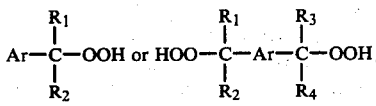

wherein Ar represents an aromatic hydrocarbon radical, and R$_1$, R$_2$, R$_3$ and R$_4$ each represent a lower alkyl group.

and topping (distilling) the resulting product consisting mainly of ketones and phenol contains tiny amounts of aldehydes. For example, the product obtained by acid-cleaving cumene hydroperoxide contains minor amounts of aliphatic aldehydes such as acetaldehyde, propionaldehyde, n-butyraldehyde and isobutyraldehyde in addition to acetone and phenol. When the acid-cleavage product is topped, and the resulting crude acetone is directly distilled, the aldehydes mix with the purified acetone, and the purity and quality of the acetone are degraded. In an attempt to remove this defect, a method was suggested which comprises adding an alkaline aqueous solution to a crude acetone containing minor amounts of aliphatic aldehydes to convert the aldehydes to higher boiling condensates by aldol condensation, then distilling the resulting product to recover an acetone fraction, and discharging the aldehydes in the form of high-boiling condensates as a distillation bottom (British Pat. No. 1,412,645, and U.S. Pat. No. 3,668,256).

The suggested method, however, causes another new trouble. When the temperature of distilling the pre-treated product is elevated in an attempt to increase the ratio of recovery of the acetone fraction, decondensation reaction of the higher boiling condensates takes place to form aldehydes again which will be included in the acetone fraction. To avoid this trouble, it is necessary to maintain the concentration of the residual acetone at about 2 to 10%. This inevitably leads to an unsatisfactory ratio of recovery of acetone, and to the increased acetone content, and therefore the increased COD (chemical oxygen demand), of the effluent.

The present inventors worked extensively in order to provide a new process for purification of aldehyde-containing ketones which is free from the aforesaid defects and suitable for commercial practice. The work led to the discovery that by hydrogenating a crude ketone containing minor amounts of aliphatic aldehydes using a palladium-containing catalyst in the presence of hydrogen and a specified amount of an active hydrogen-containing compound, the aldehydes are selectively hydrogenated to products which can be separated easily by distillation from the desired ketone; the desired ketone is not converted to the corresponding hydrogenation product, i.e. a secondary alcohol or a hydrocarbon and water, by the above catalytic hydrogenation, and therefore is not consumed by the catalytic hydrogenation; and that by distilling the so pre-treated crude ketone containing minor amount of the hydrogenation products of the aliphatic aldehydes in a customary manner, a high quality ketone having a markedly reduced content of aldehydes can be recovered at a high ratio.

In view of the fact that catalytic hydrogenation with a noble metal catalyst and hydrogen generally tends to hydrogenate not only aldehydes but also ketones although to different degrees depending upon the type of the noble metal and the reaction conditions and that with a ketone containing aldehydes in a concentration of as low as 50 to 1000 ppm, it is difficult, in the absence of an active hydrogen-containing compound, to reduce the content of the aldehydes to less than 10 ppm without substantial hydrogenation of the ketone, it is quite unexpected that by hydrogenating a crude ketone containing minor amounts of aliphatic aldehydes in the copresence of a specified active hydrogen compound using a palladium-containing catalyst which has never been suggested for use in purification of such a ketone because of the expected difficulty of avoiding the consumption of the ketone, the undesirable aldehydes are selectively hydrogenated and the amounts of the aldehydes can be reduced to below 10 ppm and the reaction can be performed without involving the consumption of the ketone, and that by distilling the resulting hydrogenation product, the ketone in a high purity can be recovered at a high recovery ratio.

It is an object of this invention therefore to provide a process for purifying a crude ketone containing minor amounts of aliphatic aldehydes to afford high purity ketone at a high recovery ratio with commercial advantage.

The above and other objects and advantages of this invention will become more apparent from the following description.

In the process of this invention, a crude ketone containing minor amounts of aliphatic aldehydes, especially crude acetone, crude methyl ethyl ketone or crude methyl isobutyl ketone containing about 50 to about 1000 ppm of aliphatic aldehydes which is obtained by the acid cleavage of an alkyl hydroperoxide is catalytically hydrogenated in the presence of hydrogen, a palladium-containing catalyst, and about 0.4 to about 15% by weight, preferably about 1 to about 5% by weight, based on the weight of the crude ketone, of an active hydrogen compound having a higher boiling point than the ketone which is selected from the group consisting of water, aliphatic alcohols containing 3 to 7 carbon atoms, alicyclic alcohols containing 5 to 8 carbon atoms, aliphatic carboxylic acids containing 1 to 6 carbon atoms and alkylamines containing an alkyl or cycloalkyl group with 5 to 9 carbon atoms.

Water is especially preferred as the active hydrogen compound. Preferably, the crude ketone is a crude acetone containing about 50 to about 1000 ppm of aliphatic aldehydes which is obtained by the acid cleavage of cumene hydroperoxide.

Examples of the other active hydrogen compounds include aliphatic alcohols containing 3 to 7 carbon atoms such as iso-propanol, butanol, pentanol, isoamyl alcohol, hexanol, octanol, isooctanol, sec.butyl alcohol, 2-pentanol, 3-pentanol, methylisopropyl carbinol, ethylisopropyl carbinol, ethyl n-propyl carbinol, methyl isobutyl carbinol, methyl sec-butyl carbinol, methyl-n-butyl carbinol, 2-hexanol, 3-hexanol, tertiary butanol, dimethylethyl carbinol, methyldiethyl carbinol, dimethylpropyl carbinol, triethyl carbinol, methylethyl propyl carbinol, dimethylbutyl carbinol, and polyols (e.g., propylene glycol, hexylene glycol, ethylene glycol, diethylene glycol, glycerol and butanediol); alicyclic alcohols containing 5 to 8 carbon atoms such as cyclopentanol, cyclohexanol, methylcyclohexanol and dimethylcyclohexanol; aliphatic carboxylic acids containing 1 to 6 carbon atoms such as formic acid, acetic acid, propionic acid, oxalic acid, succinic acid and citric acid; and alkylamines having an alkyl group or cycloalkyl group with 5 to 9 carbon atoms such as hexylamine, cyclohexylamine, methylcyclohexylamine, N-methylcyclohexylamine, N-ethylcyclohexylamine, N-ethylmethylcyclohexylamine, and dimethylcyclohexylamine.

The active hydrogen compounds used in this invention should have a higher boiling point than the ketone present in the crude ketone.

The palladium-containing catalyst used in this invention may, for example, be palladium metal, or a combination of palladium metal with a minor amount of another noble metal such as platinum or ruthenium. The use of palladium metal is especially preferred. Preferably, palladium metal is deposited on a suitable carrier such as carbon, active carbon, alumina, titanium oxide, silica, silica-alumina, or a mixture of at least two of these. Pd-carbon, Pd-alumina and Pd-titanium oxide are especially preferred.

The amount of the palladium-containing catalyst used in this invention is not critical. For example, it can be used in an amount of about 0.001 to about 1% by weight, as palladium metal, based on the weight of the crude ketone.

The process of this invention can be performed by a batchwise method or a continuous method. In either case, the amount of the catalyst can be changed as desired. For example, when the batchwise method is employed, the amount of the palladium-containing catalyst is, for example, about 0.001 to about 1% by weight, preferably about 0.002 to about 0.7% by weight, more preferably about 0.05 to about 0.3% by weight, as palladium metal based on the weight of the crude ketone. When a continuous method is employed, it is preferred to employ a fixed bed system in which hydrogen and the crude ketone can pass through a catalyst bed. The amount of the palladium-containing catalyst used in this case is, for example, about 0.002 to about 0.7% by weight, preferably about 0.01 to about 0.6% by weight, as palladium metal based on the amount of the ketone which passes the catalyst bed per hour. The space velocity of the crude ketone which passes through the catalyst layer is about 1 to about 10 $hr^{-1}$, preferably about 3 to about 10 $hr^{-1}$.

In the process of this invention, an active hydrogen compound having a higher boiling point than the crude ketone to be purified (preferably at least 10° C. higher than the latter) is used. When an active hydrogen compound having a lower boiling point than the ketone is used, it is necessary to perform an operation of removing the low boiling active hydrogen compound prior to the recovery of a ketone fraction by distillation of the hydrogenated product obtained by pre-treatment. Accordingly, the active hydrogen compound used in this invention has a higher boiling point than the ketone. In the case of treating the crude acetone for example, water, isopropanol, formic acid, and acetic acid can be used especially preferably. In particular, the utilization of water is preferred.

When the amount of the active hydrogen compound used in the process of this invention is less than about 0.4% by weight, it is difficult to reduce the aldehyde content of the crude ketone to less than 10 ppm. If the amount of the active hydrogen compound is more than about 15% by weight, especially more than about 5% by weight, an extra energy is required to separate the ketone from the active hydrogen compound. In particular, when water is used as the active hydrogen compound, the amount of the waste water increases. Accordingly, it is recommendable to use the active hydrogen compound in an amount within the above-specified range, especially about 1 to about 5% by weight based on the crude ketone.

The hydrogenation reaction is carried out at a temperature of from room temperature to about 100° C. and at a pressure of from atmospheric pressure to 10 $kg/cm^2 \cdot G$. Preferably, it is carried out at room temperature to about 60° C. and a pressure of from 1 atmosphere to 6 $kg/cm^2 \cdot G$, and more preferably, it is carried out at room temperature and one atmosphere.

The reaction time is about 1 to about 10 hours, preferably about 2 to 6 times, in the batchwise process.

The hydrogenation product obtained by the procedure described above is distilled to recover a ketone fraction. Thus, a high purity ketone having a markedly reduced content of undesirable aldehydes can be obtained at a high recovery ratio.

The pre-treatment (catalytic hydrogenation) in the process of this invention can be performed either by a fixed bed method of a fluidized bed method. When it is carried out by the fixed bed method, the hydrogenation product obtained by catalytic hydrogenation is fed into a distillation tower, and the ketone can be recovered from the top of the tower; and the active hydrogen compound having a higher boiling point than the ketone and high boiling products such as hydrogenated products of aldehydes, from the bottom of the tower.

When the process of the invention is performed in a fluidized bed, the catalyst is separated by sedimentation, filtration, centrifugal separation, etc., and then the residue can be purified in the manner described above.

The following Examples illustrate the present invention more specifically.

EXAMPLE 1

A magnetic stirrer was placed in a 1-liter three-necked flask equipped with a reflux tube through which to pass ice water, a gas introducing inlet through which to blow hydrogen gas and a sampling hole. A sealing tube filled with liquid paraffin was secured to the exit of the reflux tube so as to watch the flowing of hydrogen gas. The flask was charged with 500 ml of crude acetone containing 95 ppm of isobutyraldehyde and 200 ppm of water and 10.0 ml of water. With stirring, hydrogen gas was passed through the flask to replace the air with it. Furthermore, 10.00 g of Pd-activated carbon was added, and hydrogen gas was passed to such an extent that bubbles of hydrogen gas were observed slightly from the liquid paraffin tube at room temperature. Sampling was performed every prescribed period of time, and the unreacted isobutyraldehyde in the acetone was determined. It was 10 ppm after 1 hour, 4 ppm after 2 hours, and 4 ppm after 3 hours. The amount of isopropanol formed was below the limit (1000 ppm) of detection.

The hydrogen gas released from the reaction system was analyzed gas-chromatographically. At any stage of the reaction, no propane was detected (the limit of detection 100 ppm; calculated as weight).

After the reaction, the catalyst was separated, and the residue was distilled at atmospheric pressure at a reflux ratio of 0.5 using an Olldshaw distillation tower. Acetone which distilled out (483 ml) contained 3 ppm of isobutyraldehyde and 3000 ppm of water. As a distillation residue, 11.3 g of a high-boiling product was obtained.

EXAMPLE 2

The procedure of Example 1 was performed on the scale of 10 times. After the lapse of three hours, the acetone was distilled. The content of isobutyraldehyde in the acetone that distilled out was 3 ppm, and 4970 ml of acetone was obtained as a distillate (recovery ratio 99.4%). The acetone recovered contained 2100 ppm of water.

COMPARATIVE EXAMPLE 1

Example 1 was repeated except tha water was not added. The content of unreacted isobutyraldehyde in acetone was 36 ppm after 1 hour, 20 ppm after 2 hours, and 20 ppm after 3 hours. The amounts of isopropanol and propane formed were below the detection limits.

COMPARATIVE EXAMPLE 2

Example 1 was repeated except that 1.25 g of Raney nickel was used. After a lapse of three hours, the amount of aldehydes in the acetone was 9 ppm, and the amount of isopropanol was 1.5%. The concentration of propane in the hydrogen gas was below the extraction limit.

EXAMPLES 3 to 8

Example 1 was repeated except that each of the active hydrogen-containing compounds shown in Table 1 was used instead of water. The results obtained after a lapse of 2 hours are shown in Table 1.

Table 1

| Example | Active hydrogen-containing compound (weight %) | Unreated aldehyde (ppm) | Amount of by-product isopropanol (%) | Amount of propane (%) |
|---|---|---|---|---|
| 3 | Water (1.47) | 4 | Below the detection limit | Below the detection |
| 4 | Isopropanol (1.00) | 3 | Below the detection limit | Below the detection |
| 5 | Cyclohexanol (1.22) | 6 | Below the detection limit | Below the detection |
| 6 | Formic acid (1.54) | 5 | Below the detection limit | Below the detection |
| 7 | Acetic acid (2.60) | 5 | Below the detection limit | Below the detection |
| 8 | Cyclohexylamine (2.19) | 3 | Below the detection limit | Below the detection |

EXAMPLES 9 to 11

Example 1 was repeated except that each of the catalysts shown in Table 2 was used instead of the 5% Pd-activated carbon. The results obtained after a lapse of 2 hours are shown in Table 2.

Table 2

| Example | Catalyst | Amount of unreacted isobutyraldehyde (ppm) | Amount of by-product isopropanol (%) | Amount of propane (%) |
|---|---|---|---|---|
| 9 | 2% Pd-activated carbon | 6 | Below the detection limit | Below the detection limit |
| 10 | 5% Pd-γ-aluminum oxide | 8 | 0.3 | Below the detection limit |
| 11 | 2% Pd-titanium oxide | 2 | 0.4 | Below the detraction limit |

EXAMPLE 12

Example 1 was repeated except that crude acetone containing 580 ppm of propionaldehyde and 2000 ppm of water was used. The amount of unreacted propionaldehyde was 50 ppm after 1 hour, 12 ppm after 2 hours, and 7 ppm after 3 hours. The amounts of isopropanol and propane were below the detection limits.

EXAMPLES 13 to 17

Example 1 was repeated except that 100 ml of crude acetone containing 100 ppm of isobutyraldehyde was used instead of the crude acetone used in Example 1, water was added to it to adjust the water content of the crude acetone to the values shown in Table 3, and 2.00 g of 5% Pd-activated carbon was used and the crude acetone was heated at 51° C. The content of isobutyraldehyde in acetone determined two hours later is shown in Table 3.

Table 3

| Example | Water content (%) | Unreacted isobutyraldehyde (ppm) | By-product isopropanol (%) | Propane (%) |
|---|---|---|---|---|
| 13 | 0.4 | 8 | Below the detection level | Below the detection level |
| 14 | 1 | 8 | Below the detection level | Below the detection level |
| 15 | 5 | 9 | Below the detection | Below the detection |

Table 3-continued

| Example | Water content (%) | Unreacted iso-butyraldehyde (ppm) | By-product isopropanol (%) | Propane (%) |
|---|---|---|---|---|
| 16 | 8 | 6 | level Below the detection level | level Below the detection level |
| 17 | 12 | 6 | Below the detection level | Below the detection level |

EXAMPLE 18 (HYDROGENATION BY A CONTINUOUS PROCESS)

A cylindrical stainless steel (SUS-304) vertical reactor equipped with a jacket for temperature adjustment was used. The reactor had an inside diameter of 1 inch and a length of 308 mm. Closures of the screw type were secured to both ends of the reactor, and two sacks were fitted to the lower closure for temperature measurement. A porous plate having pores with a diameter of 3 mm was fixed to the sacks as a receiver for the filled catalyst in such a manner that the top ends of the sacks were located 50 mm and 100 mm respectively above the porous plate to permit temperature measurement of the catalyst layer and the portion above the catalyst layer. The reactor was so constructed that crude acetone mixed with hydrogen would be fed into the reactor. The reaction mixture was adapted to be introduced into a gel-liquid separator through a cooler to separate acetone from hydrogen.

Glass wool was packed on the porous receiver plate to a height of 1 cm, and 40 ml (24.4 g) of the catalyst was filled on it. Furthermore, above the catalyst layer, glass wool was again packed to a height of 1 cm.

The catalyst used was 30 to 50 mesh particles of 2% Pd-activated carbon.

Hot water was fed into the jacket of the reactor so as to adjust the temperature of the reaction system to 50° C.

Crude acetone containing 2.6% by weight of water and 100 ppm of isobutyraldehyde and hydrogen gas were fed into the reactor. The pressure of the inside of the reactor was adjusted to 5.4 kg/cm$^2$·G by hydrogen gas. The space velocity of the crude acetone which passed through the catalyst layer was 5.0 hr$^{-1}$.

The amount of isobutyraldehyde contained in the acetone obtained by the receiver was 2 ppm, and the amount of isopropanol was below the detection limit. The content of propane in the released hydrogen gas was below the detection limit.

What we claim is:

1. A process for purifying an aldehyde-containing acetone which comprises catalytically hydrogenating a crude acetone containing about 50 to about 1000 ppm of aliphatic aldehydes at a temperature of from room temperature to about 100° C. and a pressure of from atmospheric pressure to 10 kg/cm$^2$·G, in the presence of hydrogen, a palladium-containing catalyst, and about 0.4 to about 15% by weight, based on the weight of crude ketone, of water; distilling the hydrogenated product; and recovering a fraction containing the acetone.

2. The process of claim 1 wherein the amount of water is about 1 to about 5% by weight based on the weight of the crude ketone.

3. The process of claim 1 wherein the palladium-containing catalyst is palladium metal supported on a carrier.

4. The process of claim 3 wherein the carrier is selected from the group consisting of carbon, activated carbon, alumina, titanium oxide, silica, alumina silica, and mixtures of at least two of them.

5. The process of claim 1 wherein the amount of the palladium-containing catalyst is about 0.001 to about 1% by weight as palladium metal based on the weight of the crude acetone.

6. The process of claim 1 wherein the crude acetone is obtained by acid cleavage of an alkyl hydroperoxide.

7. The process of claim 1 which comprises catalytically hydrogenating crude acetone containing about 50 to about 1000 ppm of aliphatic aldehydes at a temperature of from room temperature to about 100° C. and a pressure of from atmospheric pressure to 10 kg/cm$^2$·G in the presence of hydrogen, a palladium-containing catalyst, and about 1 to about 5% by weight, based on the weight of the crude ketone, of water; distilling the resulting hydrogenation product; and recovering a fraction containing the acetone.

8. The process of claim 1 in which the hydrogenation reaction is carried out at a temperature of from room temperature to about 60° C. and a pressure of from one atmosphere to 6 kg/cm$^2$·G.

9. The process of claim 8 wherein the amount of water is about 1 to about 5% by weight based on the weight of the crude acetone.

10. The process of claim 9 wherein the palladium-containing catalyst is palladium metal supported on a carrier selected from the group consisting of carbon, activated carbon, alumina, titanium oxide, silica, alumina silica, and mixtures of at least two of these carriers, and the amount of the palladium-containing catalyst is about is about 0.001 to about 1% by weight as palladium metal based on the weight of the crude ketone.

11. The process of claim 10 wherein the hydrogenation reaction is carried out at room temperature and one atmosphere.

* * * * *